(12) United States Patent
Hara

(10) Patent No.: US 9,089,260 B2
(45) Date of Patent: Jul. 28, 2015

(54) FIXATION LAMP FOR OPHTHALMOLOGICAL INSTRUMENTS

(75) Inventor: Takuya Hara, Shizuoka-ken (JP)

(73) Assignee: Kowa Company, Ltd., Aichi (JP)

( * ) Notice: Subject to any disclaimer, the term of this patent is extended or adjusted under 35 U.S.C. 154(b) by 125 days.

(21) Appl. No.: 13/817,603

(22) PCT Filed: Aug. 8, 2011

(86) PCT No.: PCT/JP2011/068051
§ 371 (c)(1),
(2), (4) Date: Feb. 19, 2013

(87) PCT Pub. No.: WO2012/029506
PCT Pub. Date: Mar. 8, 2012

(65) Prior Publication Data
US 2013/0148082 A1 Jun. 13, 2013

(30) Foreign Application Priority Data
Sep. 2, 2010 (JP) .................. 2010-196421

(51) Int. Cl.
*A61B 3/10* (2006.01)
*A61B 3/00* (2006.01)
*A61B 3/14* (2006.01)
*F21V 21/28* (2006.01)

(52) U.S. Cl.
CPC ............. *A61B 3/0091* (2013.01); *A61B 3/0075* (2013.01); *A61B 3/14* (2013.01); *F21V 21/28* (2013.01)

(58) Field of Classification Search
USPC ................................ 351/221, 245
See application file for complete search history.

(56) References Cited

U.S. PATENT DOCUMENTS 3,601,598 A * 8/1971 Horn .............................. 362/418
3,871,753 A * 3/1975 Papritz et al. ................. 351/244

FOREIGN PATENT DOCUMENTS

| JP | 17452/1979 | 8/1980 |
| JP | 155829/1980 | 5/1982 |
| JP | 173045/1980 | 6/1982 |
| JP | 94537/1984 | 1/1986 |
| JP | 2670452 B2 | 7/1997 |

OTHER PUBLICATIONS

Int'l search report, Aug. 30, 2011, JP.

* cited by examiner

*Primary Examiner* — Ricky Mack
*Assistant Examiner* — Mustak Choudhury
(74) *Attorney, Agent, or Firm* — Duane Morris LLP

(57) ABSTRACT

[Problem] To increase, compared to conventional devices, the range of motion of the light emitter (fixation lamp) in an external fixation lamp for an ophthalmological instrument and allow movement of the light emitter to arbitrary positions. [Solution] The fixation lamp (1) has a first arm (A1), which supports a light emitter (2) and is supported by a second arm (A2) via a first joint (C1), and is configured so that the first arm (A1) is able to revolve around at least two axes of revolution (E1, E2) by means of the first joint (C1) and said axes of rotation (E1, E2) are not disposed on the same line. Thereby, the range in which the light emitter (2) can be moved can be increased compared to conventional devices and the light emitter can be moved to an arbitrary position in an arbitrary direction.

6 Claims, 4 Drawing Sheets (a)

(b)

FIXATION LAMP FOR OPHTHALMOLOGICAL INSTRUMENTS

CROSS-REFERENCE TO RELATED PATENT APPLICATIONS

The present application is a U.S. national stage application under 35 U.S.C. §371 of PCT Application No. PCT/JP2011/068051, filed Aug. 8, 2011, which claims priority to JP 2010-196421 filed on Sep. 2, 2010, the entireties of which are incorporated by reference herein.

TECHNICAL FIELD

This invention relates to a fixation lamp for ophthalmological instrument to be used in the ophtalmological instrument, such as a fundus camera and a slit lamp.

BACKGROUND ART

An external fixation lamp has been used in the ophthalmological instrument, such as a fundus camera and a slip lamp in the past (see Patent related documents 1 and 2). When visible lights are irradiated on an eye to be examined for photography and a measurement or the ophthalmological instrument does not originally have the fixation lamp (internal fixation lamp) for the eye to be examined, such an external fixation lamp is used for fixation through the other eye, that is, the eye to be photographed that is not one to be examined.

FIG. 4(a) is a side view showing an instance of a conventional structure of the fixation lamp for ophtalmological instrument, a reference numeral 100 denotes a fixation lamp, a reference numeral 101 denotes a base, a reference numeral 102 denotes a relay arm rotatably supported by the base 101, a reference numeral 103 denotes a top end arm rotatably supported by the relay arm 102, and a reference numeral 104 denotes a light emitter attached to the top end arm 103 for getting an examinee to fixate. FIG. 4(b) is a side view showing another instance of a conventional structure of the fixation lamp for ophtalmological instrument, a reference numeral 200 denotes a fixation lamp, a reference numeral 201 denotes a base pillar, a reference numeral 202 denotes a relay arm rotatably supported by the base pillar 201, a reference numeral 203 denotes a top end arm rotatably supported by the relay arm 202, a reference numeral 204 denotes a light emitter attached to the top end arm 203 for getting the examinee to fixate, and a reference numeral 205 denotes an ophtalmological instrument.

PRIOR ART

Patent Related Document

[Patent related document 1]: Japanese patent No. 2670452
[Patent related document 2]: Japanese patent application publication No. 2004-33277

SUMMARY OF INVENTION

Problems to be Solved by Invention

A structure of a conventional fixation lamp is that each arm is revolved around one axis of revolution (see arrows M1 and M2 of FIG. 4(a)), and a range of motion of the light emitter has a limit thereby. For this reason, when the light emitter is moved to a desired position, it may not be moved there. In case of FIG. 4(a), for instance, when the light emitter 104 is slightly moved in a direction perpendicular to the paper, it may not be possible.

In a case where the arm can be freely moved with no limit of the rotational angle of each arm (the rotational angle of each arm when rotating around one axis of rotation) in order to make the motion of the light emitter free and smooth, all joints has to use complex electric contacts so as not to cause such a problem that an electric wire inside the arm for supplying the light emitter with electricity may cut.

An object of the invention is to provide a fixation lamp for ophtalmological instrument that can solve the above-mentioned problem or reduce such a problem.

Means for Solving Problems

The invention according to claim 1 exemplified in FIG. 1 and FIG. 3 is a fixation lamp for ophthalmological instrument (1) that is used for getting an examinee to fixate in an ophthalmological instrument (20), comprising:
a light emitter (2) for getting an examinee to fixate;
a first arm (A1) that supports the light emitter (2);
a second arm (A2) that supports the first arm (A1) through a first joint (C1) so as to freely swing;
a base (B) that supports the light emitter (2) through the second arm (A2), the first joint (C1) and the first arm (A1);
the first joint (C1) having a first relay (D1) that is rotatably supported by the second arm (A2) and rotatably supports the first arm (A1); and
a rotation axis (E1) of the first arm (A1) that rotates in connection with the first relay (D1) and a rotation axis (E2) of the first relay (D1) that rotates in connection with the second arm (A2) not being located on the same line.

The invention according to claim 2 is the fixation lamp for ophthalmological instrument according to claim 1, wherein a rotation axis (E1) of the first arm (A1) that rotates in connection with the first relay (D1) do not pass the light emitter (2).

The invention according to claim 3 is the fixation lamp for ophthalmological instrument according to claim 1 or 2, further comprising a first stopper (not shown) provided between the first arm (A1) and the first relay (D1) so as to prevent the first arm (A1) from rotating 360 degrees or more in connection with the first relay (D1), and a second stopper (see a reference numeral K2 of FIG. 2(b)) provided between the first relay (D1) and the second arm (A2) so as to prevent the first relay (D1) from rotating 360 degrees or more in connection with the second arm (A2).

The invention according to claim 4 is the fixation lamp for ophthalmological instrument according to claim 3, wherein a second joint (C2) that is different from the first joint (C1) is located between the second arm (A2) and the base (B), the second joint (C2) is provided with a second relay (D2) that rotatably supports the second arm (A2), and the base (B) supports the second joint (C2) so as to rotate 360 degrees or more around a predetermined axis.

The invention according to claim 5 is the fixation lamp for ophthalmological instrument according to any one of claims 1 to 3, further comprising a third arm (A3) that supports the second arm (A2) through a second joint (C2) that is different from the first joint (C1) as to freely swing, wherein the second joint (C2) has a second relay (D2) rotatably supported by the third arm (A3) and rotatably supports the second arm (A2), and a rotation axis (E3) of the second arm (A2) that rotates in connection with the second relay (D2) and a rotation axis (E4) of the second relay (D2) that rotates in connection with the third arm (A3) are not located on the same line.

The invention according to claim 6 is the fixation lamp for ophthalmological instrument according to claim 5, further comprising a third stopper (not shown) provided between the second arm (A2) and the second relay (D2) so as to prevent the second arm (A2) from rotating 360 degrees or more in connection with the second relay (D2), and a fourth stopper (not shown) provided between the second relay (D2) and the third arm (A3) so as to prevent the second relay (D2) from rotating 360 degrees or more in connection with the third arm (A3).

The invention according to claim 7 is the fixation lamp for ophthalmological instrument according to claim 5 or 6, further comprising a third joint (C3) located between the third arm (A3) and the base (B), wherein the third joint (C3) has a third relay (D3) that rotatably supports the third arm (A3), and the base (B) supports the third joint (C3) so as to rotate 360 degrees or more around a predetermined axis (E6).

As detailedly shown in FIG. 2(a), the invention according to claim 8 is the fixation lamp for ophthalmological instrument according to any one of claims 1 to 7, wherein the light emitter (2) has a luminous body (2A) that emits lights by itself and a diffusion cover (2B) that diffuses lights from the luminous body (2A) so as to penetrate, located so as to cover the luminous body (2A).

The number in parentheses shows the corresponding element in the drawings for the sake of convenience, accordingly, the descriptions are not restricted and bound by the descriptions on the drawings.

Effects of Invention

According to claims 1, 4 and 8, the first arm is supported through the first joint having at least two axes of rotation so as to freely swing, and it is possible to increase the range of motion of the light emitter, compared to conventional devices, and allow movement of the light emitter to an arbitrary position thereby.

According to the invention of claim 2, if the first arm is rotated in connection with the first relay, it is possible to move the light emitter.

According to the invention of claim 3, it is possible to prevent the electric wire provided in a course of the base, the second arm, and first arm and the light emitter, for supplying the light emitter with electricity from cutting.

According to the invention of claim 5, the range of motion of the light emitter can be further increased.

According to the invention of claim 6, it is possible to prevent the electric wire from cutting in the second joint.

According to the invention of claim 7, it is possible to freely move the light emitter to a position and in a direction.

EMBODIMENTS FOR CARRYING OUT THE INVENTION

Figure 1:
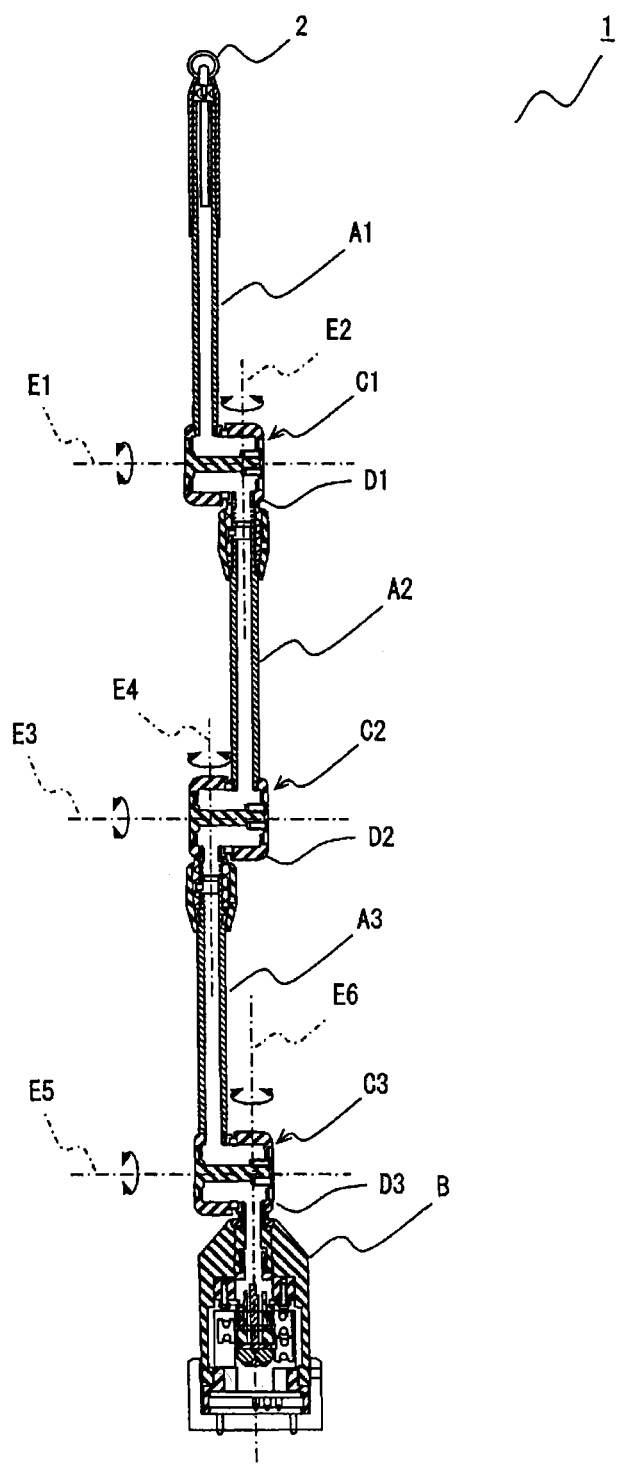
FIG. 1 is a sectional view that shows an instance of a fixation lamp for ophthalmological instrument according to the invention.
Figure 2:
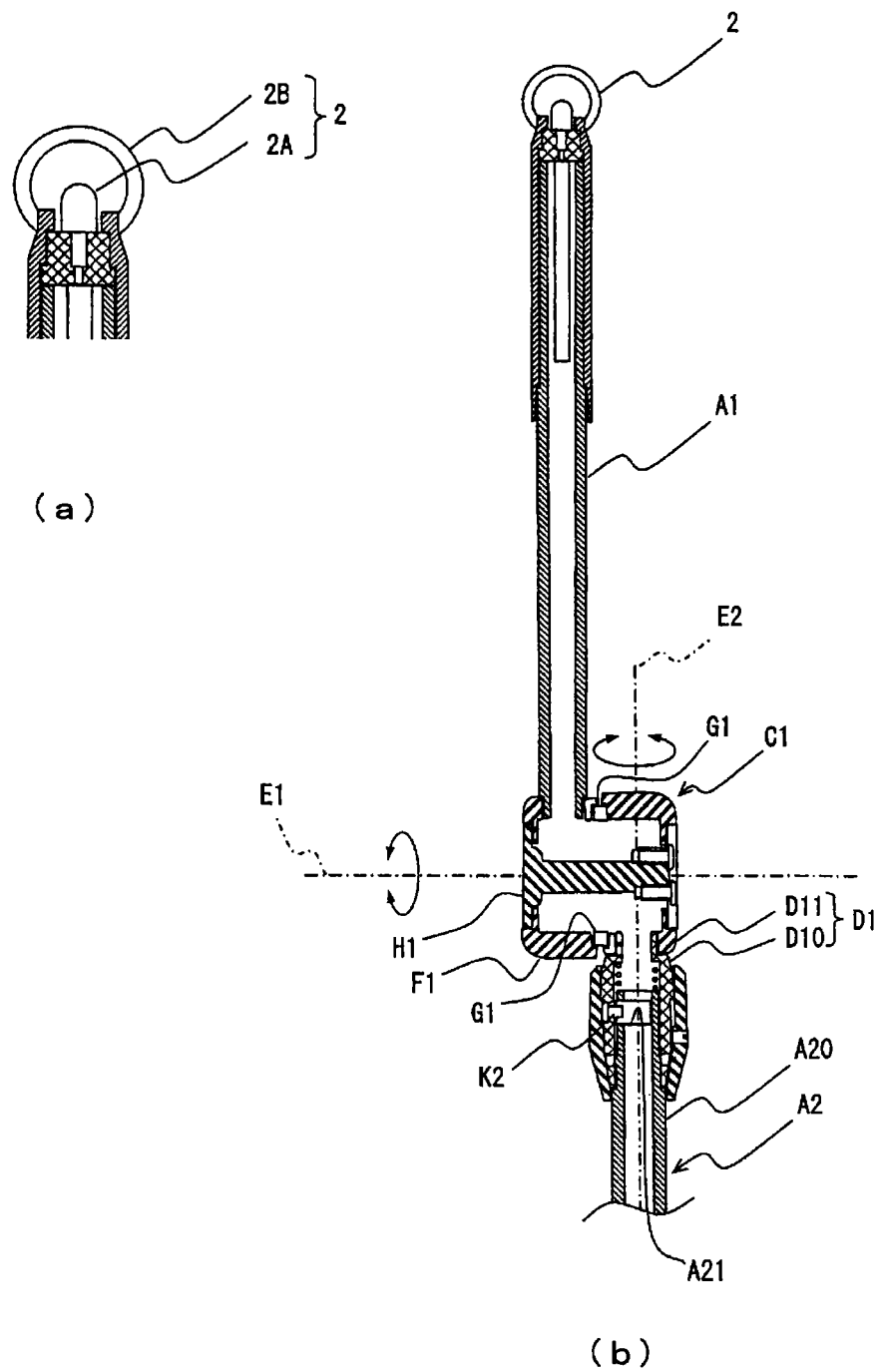
FIG. 2(a) is an enlarged sectional view that shows an instance of an light emitter.
FIG. 2(b) is an enlarged sectional view that shows an instance of a first joint.
Figure 3:
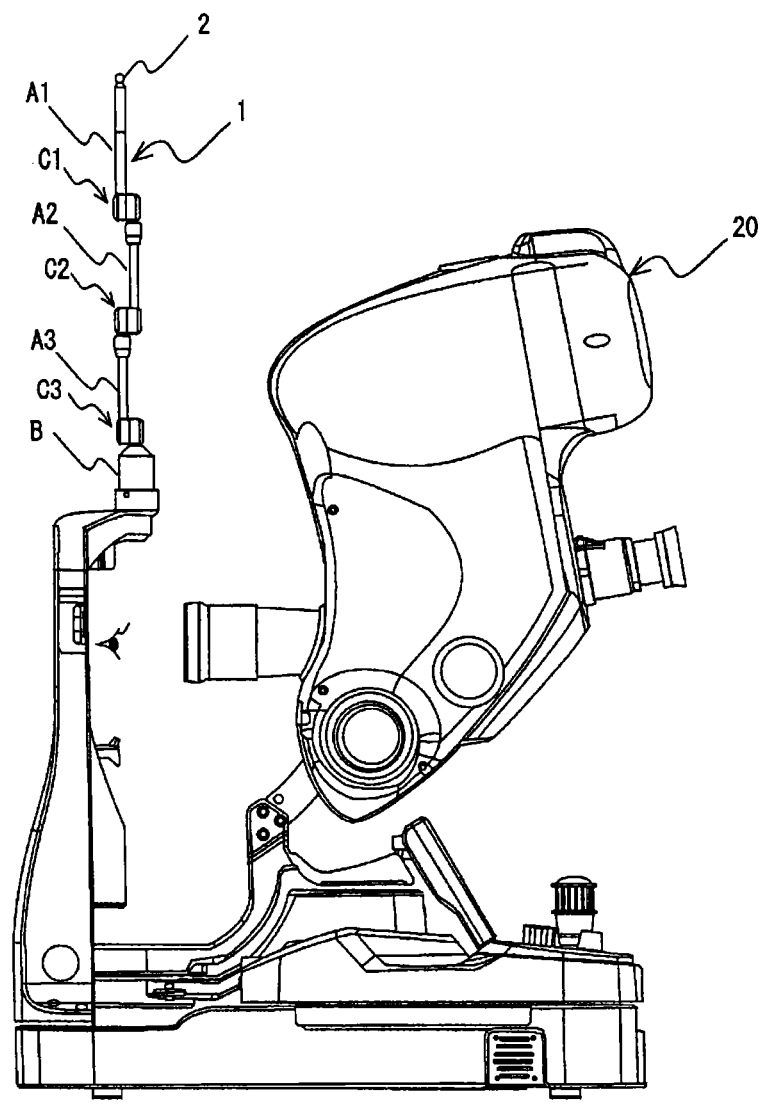
FIG. 3 is a side view that shows an instance of a use state of the fixation lamp for ophthalmological instrument according to the invention.
Figure 4:
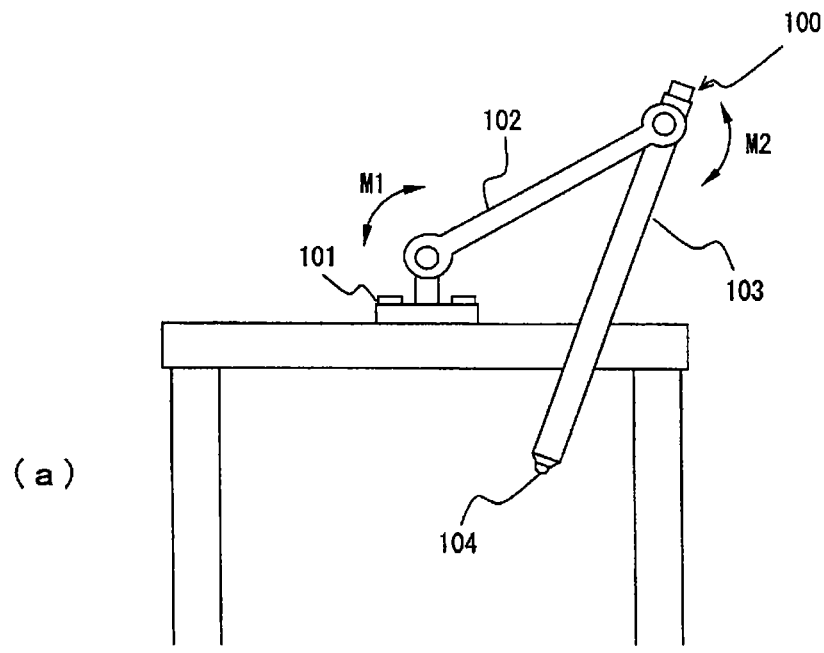
FIG. 4(a) is a side view that shows an instance of a conventional structure of the fixation lamp for ophthalmological instrument and FIG. 4(b) is a side view that shows another instance of the conventional structure of the fixation lamp for ophthalmological instrument.
Figure 4:
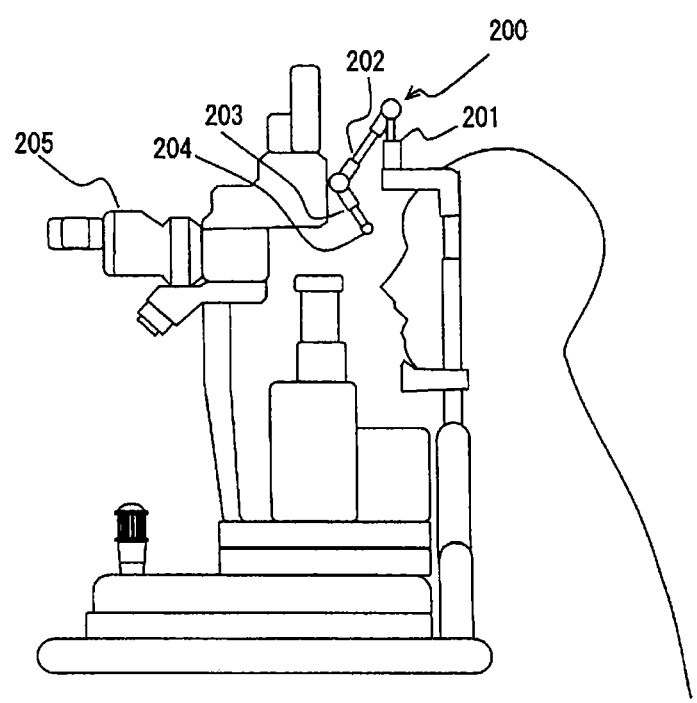

An embodiment of the invention is now explained, referring to FIGS. 1 to 3.

A fixation lamp for ophthalmological instrument 1 according to the invention as shown in FIG. 3 is a device used for ophthalmological instruments, such as fundus cameras and slit lamps, and is a device to be used in order to get examinees to fixate.

The fixation lamp for ophthalmological instrument 1 according to the invention exemplarily shown in FIG. 1 has a light emitter 2 for getting the examinee to fixate, a first arm A1 that supports the light emitter 2, a second arm A2 that supports the first arm A1 through a first joint C1 so as to freely swing, and a base B that supports the light emitter 2 through the second arm A2, the first joint C1 and the first arm A1. The above-mentioned light emitter 2 can have various kinds of shapes, but preferably, may be a object symmetrical in respective directions, such as a sphere and a regular dodecahedron. Furthermore, the light emitter 2 may protrude from a top end of the first arm A1 so as to perceive regardless of a revolution position of the first arm A1. For example as detailedly shown in FIG. 2(a), the light emitter 2 is comprised of a luminous body 2A that emits lights by itself, such as light emitting diode (LED) and a small lamp, and a diffusion cover 2B that is located so as to cover the luminous body 2A such that lights from the luminous body 2A are diffused to penetrate. And, the first arm A1 and the second arm A2 may be lighten with pipe members.

The first joint C1 is supported by the second arm A2 so as to be freely rotated, and may have a first relay D1 that rotatably supports the first arm A1. That is, such first relay D1 is connected with both the first arm A1 and the second arm A2 so as to be freely rotated. As detailedly shown in FIG. 2(b), the first relay D1 has a portion D10 in almost cylindrical shape ("the cap" hereinafter), and the cap D10 is fitted in a top end A20 of the second arm A2 so as to be freely rotated. And, the first relay D1 has a bowl-formed portion D11, and is rotatably connected with a bowl formed portion F1 via a ring member (detailedly speaking, a member made of resin in the shape of a ring). The first arm A1 is attached to the portion F1, and the first arm A1 is rotatably supported by the first relay D1 thereby. A member denoted with H1 is an omission stopper of a bowl-formed portion F11.

That is, the first arm A1 in the invention can be revolved around an axis of revolution E1 and can be also revolved around the other axis of revolution E2. The first arm A1 may be revolved around three or more axes of revolution.

As mentioned above, the first arm A1 and the first relay D1 are rotatably supported, but both may be revolved only if a predetermined force or more is added and may remain stationary if an external force is predetermined one or weaker. Otherwise, the first arm A1 and the first relay D1 may be revolved by their weights even if an external force is not given, and it may be possible to separately provide a mechanism for preventing the revolution. Any of which is available.

In the device 1 according to the invention, the axis of revolution E1 of the first arm A1 that revolves in connection with the first relay D1 and the axis of revolution E2 of the first relay D1 that revolves in connection with the first arm A2 are set so as not to be located on the same line. For example, preferably, both axes of revolution E1 and E2 may be orthogonal to each other as shown in the figure.

According to the invention, the first arm A1 is supported so as to freely swing via the first joint C1 having at least two axes of revolution E1 and E2, so that a range of motion of the light emitter 2 can be increased, compared to conventional devices, and the light emitter 2 can be moved to an arbitrary position.

In such a case, the axis of revolution E1 of the first arm A1 that rotates in connection with the first relay D1 may be set so as not to pass the light emitter 2. By doing so, the light emitter 2 can be moved by revolving the first arm A1 in connection with the first relay D1.

On the other hand, it is preferable to provide a first stopper (not shown) installed between the first arm A1 and the first relay D1 so as to prevent the first arm A1 from revolving 360 degrees or more in connection with the first relay D1, and a second stopper K2 installed between the first relay D1 and the second arm A2 so as to prevent the first relay D1 from revolving 360 degrees or more in connection with the second arm A2. Since the first arm A1 can be prevented from rotating 360 degrees or more by such a stopper, it is possible to avoid cutting of an electric wire (the electric wire provided in a course of the base B, the second arm A2, and first arm A1 and the light emitter 2, for supplying the light emitter 2 with electricity). As detailedly shown in FIG. 2(b), a notch A21 is formed at the top end A20 of the second arm A2 formed by a pipe member, and the second stopper K2 in the shape of a pin is inserted into the notch A21, being fixed by the cap D10 (that is, the first relay D1). Then, if the cap D10 is revolved around the axis of revolution E2 together with the first arm A1, the second stopper K2 that is inserted in the notch A21 also revolves, integrally, but the range of revolution (angle of revolution) of the first arm A1 is limited to a part where the notch A21 is formed. Various kinds of structures can be used to prevent the revolution of the first relay D1, but the device can be made compact and cheap with the above-mentioned structure.

The first stopper may prevent the first arm A1 from revolving 360 degrees or more, and the second stopper K2 may prevent the first relay D1 from revolving 180 degrees or more.

Preferably, without directly connecting the second arm A2 with the base B, a second joint C2 different from the first joint C1 is located between the second arm A2 and the base B, the second joint C2 is provided with a second relay D2 rotatably supporting the second arm A2, and the base B supports the second joint C2 so as to revolve 360 degrees or more around a predetermined axis of revolution.

On the other hand, the second arm A2 may be connected with the base B through a third arm A3 as shown in FIG. 1, without directly connecting the second arm A2 with the base B. In such a case, preferably, the third arm A3 supports the second arm A2 via the second joint C2 (that is, the second joint different from the first joint C1) so as to freely swing. And, the second joint C2 may have a structure similar to the first joint C1. That is, preferably, the second joint C2 is provided with the second relay D2 that is rotatably supported by the third arm A3 and rotatably supports the second arm A2. Preferably, the second joint C2 is provided with a member having a shape similar to the cap D10, a member having a shape similar to the bowl-formed portion D11, a member having a shape similar to the bowl-formed portion F1, a member having a similar shape and a similar member to the ring member G1 and a member having a shape similar to the member H1. Preferably, an axis of revolution E3 of the second arm A2 that rotates in connection with the second relay D2 and the axis of revolution E4 of the second relay D2 that rotates in connection with the third arm A3 are set so as not to locate both on the same line. By doing so, a range of motion of the light emitter 2 can be made wider.

Preferably, a third stopper (not shown) is provided between the second arm A2 and the second relay D2 in order to prevent the second arm A2 from revolving 360 degrees or more with respect to the second relay D2, and a forth stopper is provided between the second relay D2 and the third arm A3 in order to prevent the second relay D2 from revolving 360 degrees or more with respect to a third arm A3. By doing so, it is possible to avoid the cutting of an electric wire (the electric wire provided in a course of the base B, the second arm A2, and first arm A1 and the light emitter 2, for supplying the light emitter 2 with electricity) in the second joint C2.

Besides, a third joint C3 may be provided between the third arm A3 and the base B, and the third joint C3 may be provided with a third relay D3 rotatably supporting the third arm A3. In such a case, the axis of revolution of the third joint C3 may be only axis of revolution E5 in almost horizontal direction, and the revolution around the axis of revolution E6 in almost vertical direction may be done by the base B itself. In this case, the above-mentioned stopper may not be provided in the base B and electric points of contact that move may be proved so as to allow to rotate 360 degrees or more around the axis of revolution E6 (the revolution of the third joint C3). With such a structure, it is possible to freely move the light emitter 2 to a position and in a direction and freely locate the light emitter 2, and an operability of the fixation lamp can be further improved thereby.

The fixation lamp for ophthalmological instrument to be used for getting the examinee to fixate in the ophthalmological instrument may have the light emitter 2 for getting the examinee to fixate, the first arm A1 for supporting the light emitter 2, the second arm A2 for supporting the first arm through the first joint C1 so as to freely swing, the base B for supporting the light emitter 2 through the second arm A2, the first joint C1 and the first arm A1, and the light emitter 2 may have the luminous body 2A that emits lights by itself and the diffusion cover 2B located, covering the luminous body 2A, for diffusing lights from the luminous body 2A so as to penetrate. The above-mentioned light emitter 2 may have various kinds of shapes, and preferably, is an object symmetrical in respective directions, such as a sphere or a regular dodecahedron. Furthermore, the light emitter 2 may protrude from the top end of the first arm A1 so that a person can watch regardless of the rotational position of the first arm A1.

EXPLANATION OF REFERENCE NUMBERS

1 . . . fixation lamp for ophthalmological instrument
2 . . . light emitter
20 . . . ophthalmological instrument
A1 . . . first arm
A2 . . . second arm
A3 . . . third arm
B . . . base
C1 . . . first joint
C2 . . . second joint
C3 . . . third joint
D1 . . . first relay
D2 . . . second relay
D3 . . . third relay
E1, E2, E3, E4 . . . axis of revolution
K2 . . . second stopper

The invention claimed is:
1. A fixation lamp for ophthalmological instrument that is used for getting an examinee to fixate in an ophthalmological instrument, comprising:
a light emitter for getting an examinee to fixate;
a first arm having a top end and a second end, wherein the light emitter is provided on the top end and protrudes from the top end;

a second arm that supports the first arm through a first joint that connects the second arm to the second end of the first arm, the first joint allowing the first arm to freely swing;

a base that supports the light emitter through the second arm, the first joint and the first arm;

the first joint having a first relay that is rotatably supported by the second arm and rotatably supports the first arm;

a first stopper provided between the first arm and the first relay and preventing the first arm from rotating 360 degrees or more in connection with the first relay;

a second stopper provided between the first relay and the second arm and preventing the first relay from rotating 360 degrees or more in connection with the second arm; and a rotation axis of the first arm that rotates in connection with the first relay and a rotation axis of the first relay that rotates in connection with the second arm not being located on the same line, wherein a second joint that is different from the first joint is located between the second arm and the base, the second joint is provided with a second relay that rotatably supports the second arm, and the base supports the second joint allowing the second joint to rotate 360 degrees or more around a predetermined axis.

2. The fixation lamp for ophthalmological instrument according to claim 1, wherein the light emitter has a luminous body that emits lights by itself and a diffusion cover that diffuses lights from the luminous body so as to penetrate, located so as to cover the luminous body.

3. A fixation lamp for ophthalmological instrument that is used for getting an examinee to fixate in an ophthalmological instrument, comprising:

a light emitter for getting an examinee to fixate;

a first arm having a top end and a second end, wherein the light emitter is provided on the top end and protrudes from the top end;

a second arm that supports the first arm through a first joint that connects the second arm to the second end of the first arm, the first joint allowing the first arm to freely swing, the first joint having a first relay that is rotatably supported by the second arm and rotatably supports the first arm;

a first stopper provided between the first arm and the first relay and preventing the first arm from rotating 360 degrees or more in connection with the first relay;

a second stopper provided between the first relay and the second arm and preventing the first relay from rotating 360 degrees or more in connection with the second arm;

a rotation axis of the first arm that rotates in connection with the first relay and a rotation axis of the first relay that rotates in connection with the second arm not being located on the same line;

a third arm that supports the second arm through a second joint that is different from the first joint the second joint allowing the second arm to freely swing, wherein the second joint has a second relay rotatably supported by the third arm and rotatably supports the second arm, and a rotation axis of the second arm that rotates in connection with the second relay and a rotation axis of the second relay that rotates in connection with the third arm are not located on the same line; and a base supporting the third arm.

4. The fixation lamp for ophthalmological instrument according to claim 3, further comprising a third stopper provided between the second arm and the second relay so as to prevent the second arm from rotating 360 degrees or more in connection with the second relay, and a fourth stopper provided between the second relay and the third arm so as to prevent the second relay from rotating 360 degrees or more in connection with the third arm.

5. The fixation lamp for ophthalmological instrument according to claim 3, further comprising a third joint located between the third arm and the base, wherein the third joint has a third relay that rotatably supports the third arm, and the base supports the third joint so as to rotate 360 degrees or more around a predetermined axis.

6. The fixation lamp for ophthalmological instrument according to claim 3, wherein the light emitter has a luminous body that emits lights by itself and a diffusion cover that diffuses lights from the luminous body so as to penetrate, located so as to cover the luminous body.

* * * * *